United States Patent [19]

Babington

[11] 4,228,795
[45] Oct. 21, 1980

[54] APPARATUS FOR PRODUCING FINELY DIVIDED LIQUID SPRAY

[76] Inventor: Robert S. Babington, 1113 Ingleside Ave., McLean, Va. 22101

[21] Appl. No.: 775,494

[22] Filed: Mar. 8, 1977

[51] Int. Cl.² .................... B05B 11/04; B05B 11/06
[52] U.S. Cl. ........................... 128/200.22; 239/338; 239/346
[58] Field of Search ............. 239/337, 338, 343, 346, 239/432, 433; 128/193, 194, DIG. 2; 261/78 A, DIG. 65

[56] References Cited

U.S. PATENT DOCUMENTS

| | | | |
|---|---|---|---|
| 643,014 | 2/1900 | Tatum | 239/338 |
| 1,263,079 | 4/1918 | Leon | 239/338 |
| 1,839,193 | 1/1932 | Blanchard | 239/338 X |
| 2,274,669 | 3/1942 | Curry | 239/338 |
| 2,330,297 | 9/1943 | Lynch | 261/78 A |
| 3,421,699 | 1/1969 | Babington et al. | 239/337 |
| 3,506,589 | 4/1970 | Hoffman et al. | 261/78 A |
| 3,664,337 | 5/1972 | Lindsey et al. | 128/194 |
| 3,709,433 | 1/1973 | Obergefell et al. | 239/338 |
| 3,809,080 | 5/1974 | Deaton | 261/DIG. 65 X |
| 3,864,326 | 2/1975 | Babington | 239/337 X |

*Primary Examiner*—Robert W. Saifer
*Attorney, Agent, or Firm*—Pollock, Vande Sande and Priddy

[57] ABSTRACT

Apparatus for producing finely divided liquid particles which includes two chambers having means for conveying liquid from one chamber to the other and back again to the first chamber in response to a means for producing a pressure differential between the chambers. A hollow apertured plenum chamber having a smooth outer surface is positioned so that the liquid impinges on its exterior surface as it traverses its flow path. Gas is supplied under pressure to the interior of the plenum and ruptures the thin film of liquid at the aperture to produce the finely divided liquid particles.

54 Claims, 9 Drawing Figures

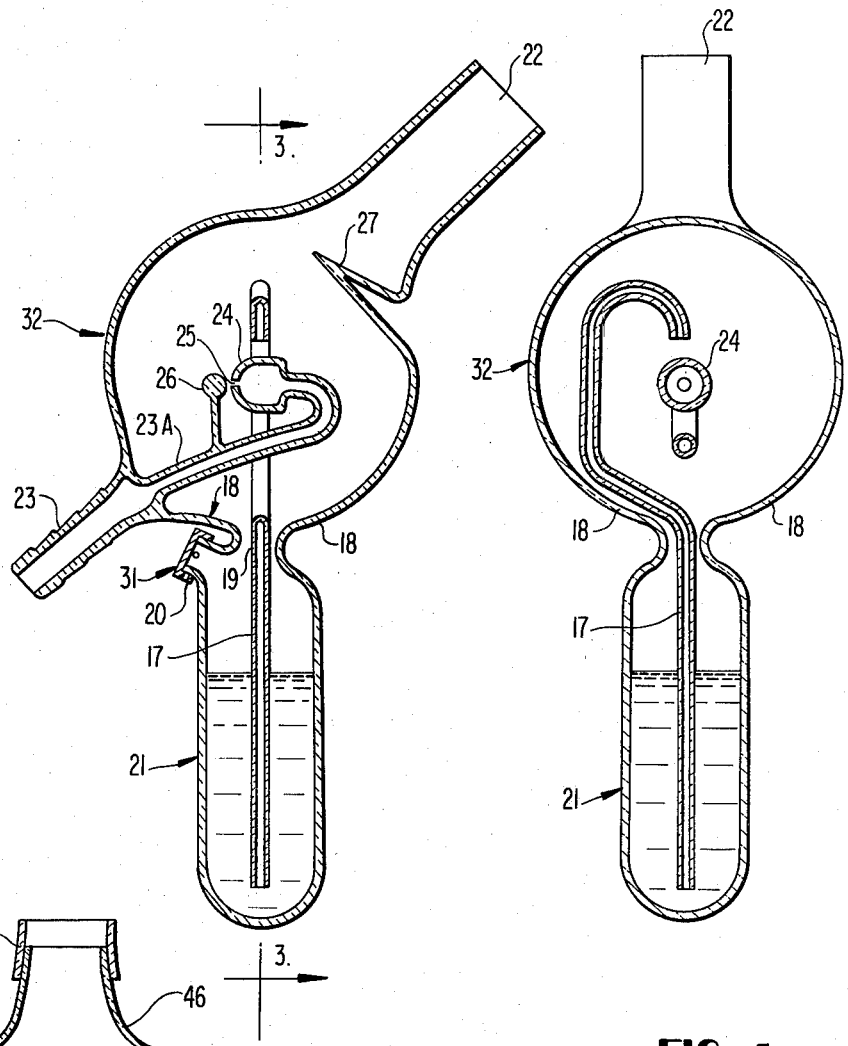

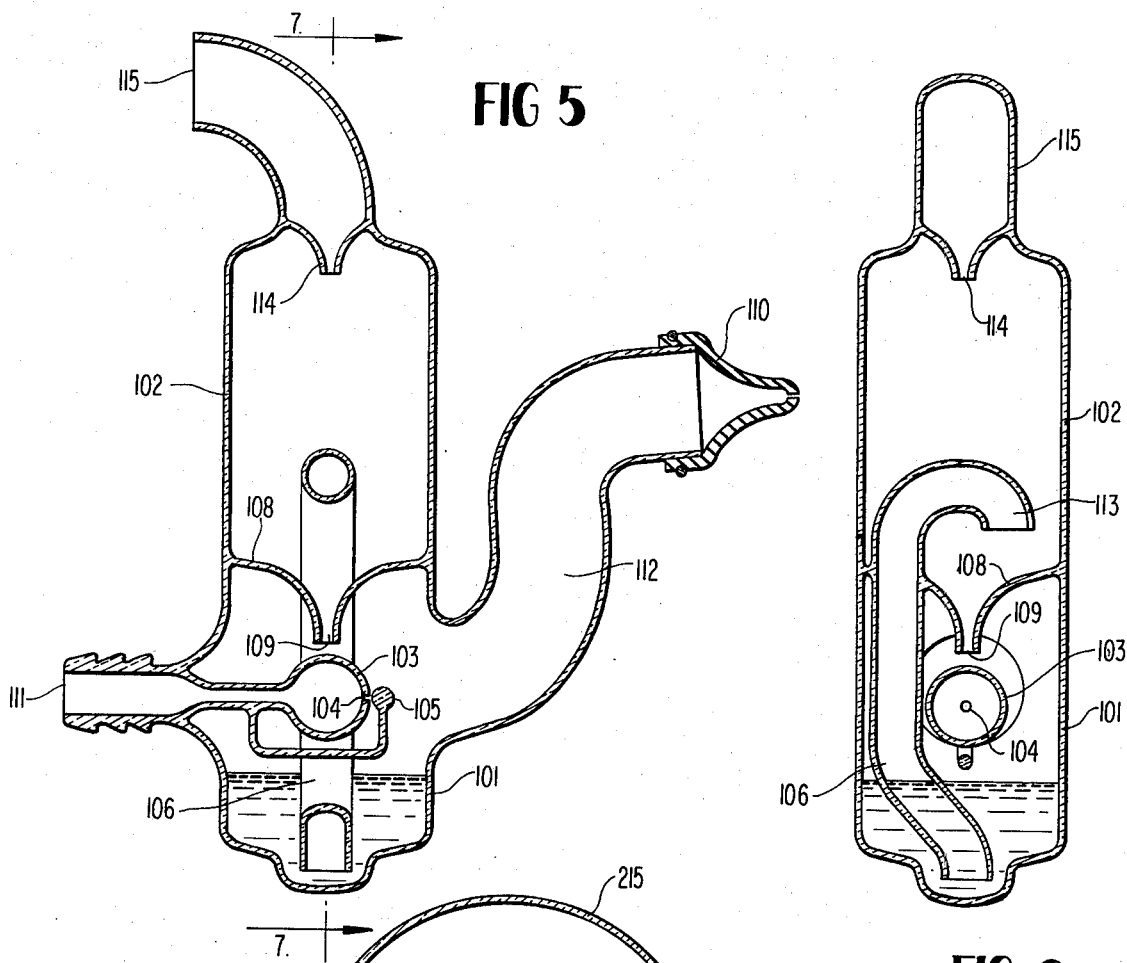
FIG 5
FIG 6
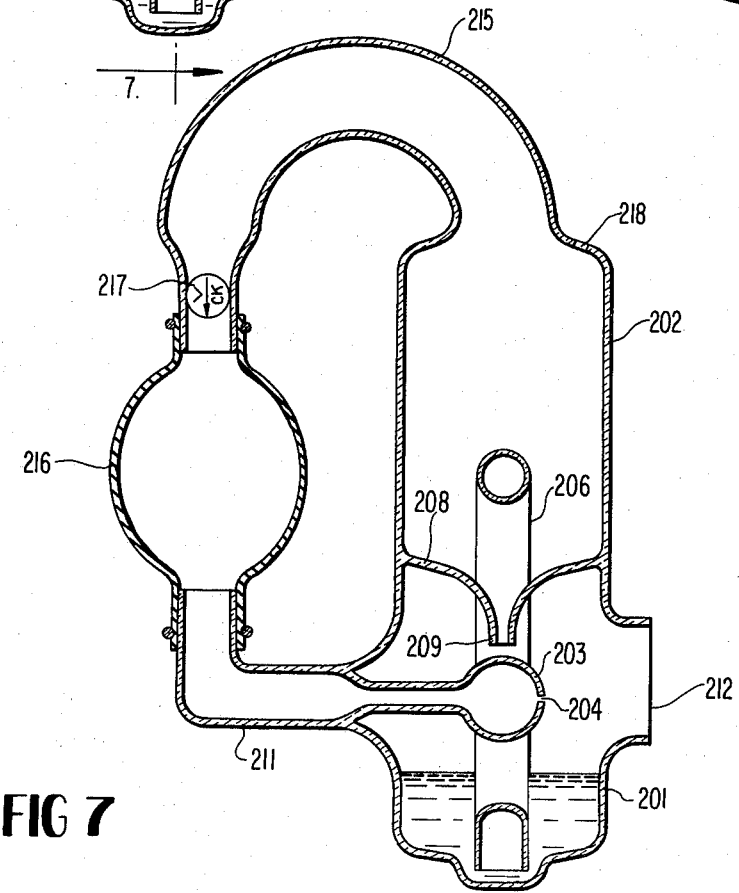
FIG 7

FIG 8

APPARATUS FOR PRODUCING FINELY DIVIDED LIQUID SPRAY

BACKGROUND AND PRIOR ART

The present invention is concerned with apparatus for producing finely divided liquid particles for household, industrial and medical spraying applications. The invention is particularly useful in the field of respiratory inhalation therapy.

A device that disperses liquid into a fine spray or aerosol, used for medical purposes, is often called a nebulizer. When the aerosol output from a nebulizer is conveyed to a patient through a flexible conduit or hose so that he can inhale the nebulizer output through either a face mask or a face tent, the patient is said to be receiving inhalation respiratory therapy. In other applications, the patient may be totally immersed in a mist tent so that his entire body, or at least the head and trunk, is surrounded by the aerosol. In still other cases, the patient may inhale the nebulizer output directly from a mouthpiece.

Until recently, there were only two means of producing aerosols for medical purposes. The Bernoulli principle was the first technique that was used, and most conventional pneumatic sprayers, atomizers and nebulizers utilize this principle. A substantial improvement was realized with the advent of the ultrasonic principle of atomization. While the ultrasonic nebulizer produces a superior aerosol as compared to conventional pneumatic systems, it is an expensive device using electronic components and thus may not be wholly dependable in service.

The most recent improvement uses what is now referred to as the Babington principle, descriptions of which can be found in U.S. Pat. Nos. 3,421,692, 3,421,699, 3,425,058, 3,425,059, 3,504,859 and 3,864,326. Some articles of interest describing utilization of this principle and its advantages in several publications include: *The Babington Nebulizer: A New Principle for Generation of Therapeutic Aerosols* by Mitchell Litt et al, appearing in the *American Review of Respiratory Disease*, Volume 105, Number 2, February 1972, pages 308–310; *Popular Science, Clog-Proof Super Spray Oil Burner Saves Fuel Costs Two Ways* by Norman Metzger, and appearing in *Popular Science*, January 1976, pages 64–67; and *What Makes Coffee Coffee-er, Houses Cozier Breathing Easier, It's Superspray* by Simon Dresner, and appearing in *Popular Science*, May 1973. Medical nebulizers that utilize the Babington principle are now being commercially used in the United States and parts of Europe.

Nebulizers employing the Babington principle provide flexibility in all of the important performance parameters such as operating flow range, nebulizer output capacity, and liquid particle size. Such nebulizers are also capable of producing an almost constant aerosol density throughout their wide range of operation. The flow range of atomized liquid plus gas may be varied from a minimum of about 5 liters per minute in one model to a maximum of about 300 liters per minute in another model. Output capacity of liquid vaporized in these units can also be varied from 0.2 cc/minute to 7 cc/minute. Since there are no moving or electronic parts to overheat, the mist is delivered at a cooler temperature which, in turn, provides for reduced condensation due to cooling on the walls of outlet conduits. Also, these nebulizers achieve optimum performance immediately, with no warm-up time required, an obvious advantage in a 15 to 20-minute treatment.

Clinicians generally agree that a particle size with a mass median diameter of 5 microns and below is the most beneficial from a therapeutic point of view. Nebulizers utilizing the Babington principle produce a spray wherein the liquid particle size falls within this desired range. Such nebulizers are easy to maintain and safe to use, particularly since they do not have any moving parts to wear out. They can also be quickly assembled and disassembled, and are safe to use with no chance of electrical malfunctions.

SUMMARY OF THE INVENTION

The present invention is concerned with apparatus for producing a finely divided liquid spray which includes two chambers, one of which holds a supply of liquid to be atomized. Means are provided for conveying the liquid from one chamber to another chamber and back to the chamber from which it originated. In order to convey the liquid from one chamber to the other and back, there is provided means for producing a pressure differential between the two chambers. The apparatus also contains a hollow plenum chamber which has a smooth outer surface over at least a portion thereof. The plenum is located in such a manner that the liquid impinges on its exterior surface as it traverses its flow path. Means are provided for introducing gas under pressure to the interior of the plenum chamber, and this gas escapes through an aperture in the plenum and thereby ruptures the liquid film at the aperture to cause a dispersion of finely divided liquid particles. An outlet is provided for the finely divided liquid particles.

Medical nebulizers constructed in accordance with the present invention provide several advantages over those made in accordance with those disclosed in the aforementioned patents, particularly U.S. Pat. No. 3,864,326. Thus, in accordance with the present invention, a pressure differential is produced in the two chambers to convey the liquid over its flow path. This makes it possible to provide a steady stream of liquid over the plenum, at least for a time as distinguished from the bubble-type of pumping means disclosed in U.S. Pat. No. 3,864,326 which employs bubbles of gas to pump the liquid which, in turn, produces a nonsolid liquid stream broken by gas bubbles.

Also, the presently commercially available line of nebulizers using the Babington concept is designed to operate primarily with water and saline solutions and in some cases with a propylene glycol additive. They are not designed to dispense small dose volumes of liquid and are not particularly suited for dispersing certain viscous liquids or sticky medications. In contrast, the apparatus of this invention is highly suited for spraying viscous or sticky liquids such as medicaments, hair sprays, and the like.

Also, the apparatus of the present invention is capable of atomizing small volumes of liquid on a periodic or intermittent basis and at precisely the time desired by, or beneficial to, the user. The size of the apparatus can be such as to be held conveniently in the hand.

Devices now on the market which are designed to provide medication in intermittent small dosages suffer from a number of disadvantages. These devices usually contain a bronchodialator such as Epinephrine in a supposedly inert propellant such as Freon. When desiring relief, the user places the mouthpiece in his mouth and inhales, while simultaneously depressing a button which releases a combined dosage of medication and aerosol propellant. In this type of treatment, an improper dosage can be easily administered, especially if the hand coordination of the user is not properly synchronized with his breathing rhythm. This type of aerosol spray device has also come under recent criticism by the U.S.F.D.A. because of the potential danger of using Freon propellants in therapeutic applications.

In other types of spray devices, the spray is dispensed from a resilient or collapsible container that is vigorously squeezed to provide the necessary pressure to disperse the liquid.

In still another type of device, the patient fills a small hand held nebulizer with medication, attaches the unit to a compressed gas source, and repeatedly inhales until the medicine has been used. The disadvantages associated with these prior art type devices can be overcome by the present invention which provides aerosol apparatus suitable for administering intermittent and small dose aerosols.

Providing aerosol therapy to a patient who is being kept alive by a ventilator or respirator poses still another problem. In this situation, the patient is unable to breathe for himself, and the prescribed medication must be forced into his lungs in conjunction with the operation of the life support equipment. In still other cases, a fine aerosol must be delivered deep into the lower airways of the lungs of a patient whose lungs are so damaged that he or she cannot breathe deeply without assistance. In both these cases, the medication must be driven into the patient's mouth with an intermittent positive pressure breathing apparatus (IPPB). The apparatus of this invention is particularly adapted to be used with such life support equipment.

An additional advantage of the present invention is that it does not waste the liquid to be sprayed as do many of the nebulizers currently available on the market. This is particularly important in view of the high cost of the medications that may be used in respiratory therapy.

As will be clearly apparent to persons skilled in the art, the present invention is also applicable to spray apparatus suitable for many portable household and industrial spraying applications.

BRIEF DESCRIPTION OF THE DRAWINGS

In describing the invention, reference will be made to the accompanying drawings in which like reference characters represent corresponding parts in the several views and in which:

FIG. 1 is a schematic, elevational section view of an embodiment of the present invention;

FIG. 2 is a sectional view taken along line 3—3 of FIG. 1;

FIG. 3 is a schematic, elevational section view of another embodiment of the present invention;

FIG. 4 is a schematic, elevational sectional view of a further embodiment of the present invention;

FIG. 5 is a schematic, elevational sectional view of still a further embodiment of the present invention;

FIG. 6 is a sectional taken along line 7—7 of FIG. 5;

FIG. 7 is a schematic elevational sectional view of another embodiment of the present invention; and FIG. 8 is a schematic elevational sectional view of a further embodiment of the present invention.

DETAILED DESCRIPTION OF PREFERRED EMBODIMENTS

THE EMBODIMENT OF FIGS. 1 AND 2

Figure 9:
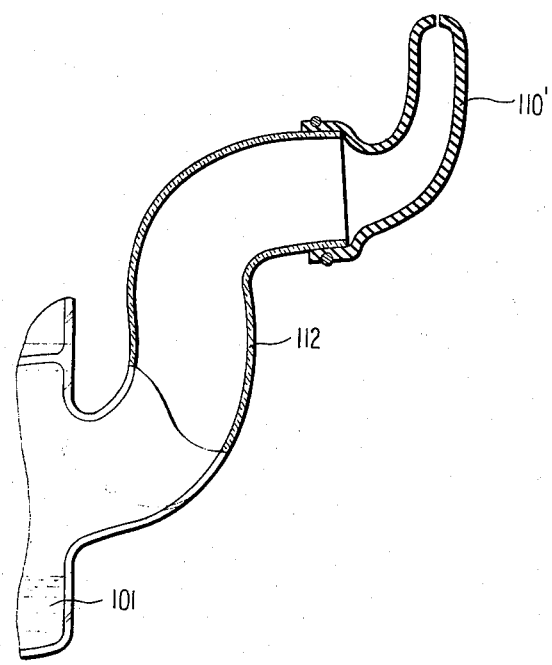
FIG. 9 is a schematic elevational sectional view of a device suitable for nose inhalation.

In the embodiment of FIGS. 1 and 2, the atomizer includes an upper chamber 32 and a lower chamber 21, the two chambers being in communication via a lift tube 17 and a return aperture 19 passing through wall segment 18 which separates the two chambers. Also communicating with lower chamber 21 is an outlet vent 20 provided with an aspirator control cap 31 the function of which will later be described. The upper chamber 32 terminates in a discharge opening 22, and also houses a hollow plenum chamber 24 having a small aperture 25. Aerosol outlet baffle means 27 is also provided in upper chamber 32. Gas, such as air, under pressure is admitted to the plenum 24 via fitting 23 connected to plenum 24 by pressure conduit 23A. A continuous gas service can be connected to fitting 23, or the pressurization of plenum 24 can be accomplished by means of a hand-manipulated squeeze bulb or squeeze container.

Since the atomizer shown in FIGS. 1 and 2 has particular advantages as a medical nebulizer, it is illustrated with an impactor 26 disposed directly in the discharge path of the gas emitting from aperture 25 in plenum 24. This impactor arrangement and its function are disclosed in my U.S. Pat. No. 3,864,326, the disclosure of which is incorporated herein by reference.

The operation of this embodiment of the present invention is as follows:

Lower chamber 21 is charged with a liquid such as a medication that is normally used in inhalation therapy practice.

Compressed gas such as air or oxygen is supplied to fitting 23 so as to pressurize plenum 24 and cause a jet of pressurized gas to emit from orifice 25. The patient places opening 22 in his mouth and inhales. This creates a vacuum in upper chamber 32. During the inhalation phase of operation, room air is drawn into lower chamber 21 through vent 20 to maintain atmospheric pressure in lower chamber 21. The resulting pressure differential between chambers 21 and 32 results in a flow of liquid from lower chamber 21 to upper chamber 32 via lift tube 7. The liquid impinges on plenum 24 in the vicinity of its north pole to create a thin film over the surface of the plenum particularly adjacent its equator where aperture 25 is located. The film is shattered by the jet of compressed gas escaping from orifice 25, which causes a dispersion of fine liquid particles which are drawn into the patient's mouth. Baffle means 27 serves to arrest the carry over of any large particles and direct them back to chamber 32 for subsequent re-atomization. In the embodiment shown in FIGS. 1 and 2, impactor 26 is located in front of orifice 25 to further reduce the particle size of the final aerosol. In most cases, the inhalation medicant nebulizer would incorporate an impactor means because in respiratory therapy applications, the preferred aerosol particle size is normally 5 microns or less and this can best be achieved using an impactor.

Optionally, the atomizer may also contain an air aspirator control means 31, affixed to the outlet of vent 20. When aspirator cap 31 is manipulated to restrict the flow of room air into lower chamber 21, the patient must inhale more deeply to receive the desired amount of medication in aerosol form. Such inducement to deep breathing can be quite desirable when a patient is inhaling aerosols for therapeutic purposes. During inhalation, there is a flow of air through aperture 19 which prevents the flow of run-off liquid from the upper chamber to the lower chamber. When the patient completes the inhalation cycle of his breathing, and removes opening 22 from his mouth, both chambers become open to atmospheric pressure, the upper chamber being vented by opening 22 and the lower chamber via vent 20 and aspirator control 31. As a result, the overflow medicant liquid that has been trapped in the upper reservoir 32 during inhalation now flows by gravity back into lower chamber 21. In order for return aperture 19 to serve as an aerodynamic closure means in the manner just described, it must be small enough to allow the patient to suck a vacuum in upper chamber 32 such that said vacuum is sufficient to promote the proper flow of liquid medicant over atomizing plenum 24. If aperture 19 were too large, the similarly large flow of atmospheric air into lower chamber 21 via vent 20 and through aperture 19 would prevent the creation of a sufficient vacuum in upper chamber 32. On the other hand, if aperture 19 were tightly constricted to make it easier for the patient to pull a vacuum in upper chamber 32, the aperture might be too small to allow the passage of certain sticky medicants to flow into lower chamber 21 after the inhalation cycle has been completed. The proper size of aperture 19 can readily be determined by those skilled in the art without undue experimentation.

In some cases, a patient receiving inhalation therapy is provided with a specified medicant dose (e.g., 10 cc.) and asked to continue inhaling until all the medicant dose is gone. In such a case, the patient may wish to keep opening 22 in his mouth, in which event, the patient may also exhale into the opening 22. This will further pressurize upper chamber 32 and assist the drainback of excess fluid through return aperture 19.

In the described operation, the atomizer will respond to the negative and positive pressures created by the respiratory rhythm of the patient and liquid will alternately flow from lower chamber to upper chamber and then back again to the lower chamber, with the return aperture 19 acting as an aerodynamic closure means to allow the passage of air upwardly into chamber 32 upon inhalation and the flow of liquid downwardly into lower chamber 21 during exhalation.

In this embodiment, the spray output and the particle size of the resultant mist may be controlled by the size and shape of baffle 27, and by varying the location of the outlet end of lift tube 17 with respect to plenum 24 and aperture 25.

In the mode of operation just described, the needed pressure differential between upper chamber 32 and lower chamber 21 is created by the inhalation of a patient. In cases where a patient is unconscious or cannot inhale in a manner sufficient to cause the necessary pressure differential between the two chambers, the embodiment shown in FIG. 1 can be operated by supplying a positive pressure to lower chamber 21 via vent port 20. When used in medical applications, this positive pressure might well be supplied by a respirator or ventilator. In such cases, the patient unable to breathe for himself could still receive aerosol treatments as the life support equipment alternately pressurizes lower chamber 21 in a precise breathing rhythm, to force air and aerosol into the patient's respiratory tract via opening 22 in upper chamber 32.

If the outlet opening 22 were made smaller, such that it could be placed in the nostril of a person, the embodiment shown in FIG. 1 could become a very effective nasal spray device. In this case the needed vacuum in upper chamber 32 would be created by inhalation through a patient's nose rather than by inhalation through a patient's mouth.

THE EMBODIMENTS OF FIGS. 3 AND 4

FIGS. 3 and 4 illustrate two embodiments intended to operate by the squeezing action of the user's hand while manipulating a conventional squeeze bulb or while depressing a collapsible liquid container to create the necessary pressure not only to cause liquid transfer between the chambers but also to supply air under pressure to the atomizing plenum chamber.

As shown in FIG. 3, the apparatus is divided by partition 49 into upper and lower chambers 52 and 40. The partition 49 is traversed by a return port 53 and a pressure conduit 42 having a by-pass aperture 41 exhausting into lower chamber 40. A baffle 54 is disposed above the return port in aperture 53. The pressure conduit 42 terminates in the upper chamber 52 in a hollow convex plenum chamber 43 having an aperture 44 located approximately at its highest elevation and directed towards discharge opening 46 provided in the top of chamber 52. In this embodiment, the cross sectional area of discharge opening 46 may be varied by means of a suitable nozzle extension 57 which may be in the form of a push/pull extension, a revolvable collar, or some other suitable control means. Chamber 52 is also provided with an atmospheric inlet port 50 which may be opened or closed to provide variations in the output spray capacity and spray pattern.

Lift tube 45 which also communicates between the two chambers 40 and 52 has a lower end disposed in the bottom of lower chamber 40, while its upper end protrudes into an extension conduit 48. This allows upper end 51 of said extension conduit to be moved up or down at the discretion of the user by any suitable means not shown. In FIG. 3, upper end 51 is shown striking the bullet shaped plenum 43 where the hemispherical tip meets the cylindrical cross section of pressure conduit 42. It is fully intended however, that extension conduit 48 be capable of simple adjustments such that the flow of liquid exiting from upper end 51 of extension conduit 48 can be caused to strike plenum 43 at any location below aperture 44, and even at locations below the juncture of convex plenum 43 and pressure conduit 42. By adjusting the location of end 51 with respect to plenum 43, the liquid film thickness may be varied which in turn allows the size of the liquid spray particles to be controlled. Further adjustments in liquid particle size can be made by varying the cross sectional area of discharge opening 46 by means of a revolvable collar 57 or the like, or by changing the length of discharge opening 46 by means of a nozzle extension 57. For example, if the cross sectional area of discharge opening 46 is reduced or its length is increased, this more tortuous path will serve to arrest the larger liquid particles in the spray output, and direct them back into upper chamber 52. In the absence of these larger particles, the resulting spray will become finer. Similarly by shortening the length of discharge opening 46 or by increasing its cross sectional area, a coarser spray can be generated.

The operation of this variation of the basic apparatus is as follows:

A conventional squeeze bulb 55 of the type that contains a mechanical check valve 56 in its suction side is attached to fitting 47 and the liquid to be sprayed is placed in lower chamber 40. When the bulb is squeezed, its checkvalve 56 closes in response to the pressure rise within the bulb and a supply of compressed air is delivered to the interior of atomizing plenum 43 via pressure conduit 42. Also, in communication with pressure conduit 42 is by-pass aperture 41. This aperture is precisely ported to pass the necessary airflow and thus provide the needed pressure rise within lower chamber 40 to simultaneously force liquid from chamber 40 to upper chamber 52 via tube 45 and extension conduit 48. The liquid pumped into chamber 52 and exiting from end 51 spreads out in a thin film over plenum 43 and is ruptured by the jet of gas escaping from orifice 44, causing a spray of finely divided particles. In this embodiment, the squeeze bulb serves to simultaneously pressurize the lower chamber 40 as well as the atomizing plenum 43.

When the squeeze bulb is released, it is recharged with atmospheric air partially by air entering the squeeze bulb via its checkvalve. However, additional atmospheric air is also sucked into the squeeze bulb upon its release, said additional air being aspirated through orifice 44 in plenum 43 and through by-pass aperture 41. As a result, a slight vacuum is created in lower chamber 40 which helps to promote the flow of liquid from upper chamber 52 back into lower chamber 40.

If an alternate type of conventional squeeze bulb is used, namely the closed type that does not contain an inlet checkvalve, the flow of liquid from upper chamber 52 to lower chamber 40 can be further accelerated. With the closed type squeeze bulb, operation will be precisely as described during the pressure cycle when the bulb is squeezed. However, when the bulb is released, and in the absence of an inlet checkvalve, all of the air needed to recharge the bulb will, by necessity, be drawn in through orifice 44 in plenum 43 and through by-pass aperture 41 in conduit 42 which communicates with atmospheric air via return port 53 and discharge horn 46. This will create a much stronger vacuum in lower chamber 40 than in the earlier described arrangement, and said vacuum will promote faster drainage of liquid from upper chamber 52 to lower chamber 40.

During the pressurization portion of the cycle, that portion of the liquid that is not sprayed off drains downwardly along the outside surface of main pressure conduit 42, which is affixed to partition 49. Under normal operating conditions it will take longer for the excess liquid to drain down along the main air supply line 42 and reach aperture 53 than it does for the pressurization cycle to be completed. This means that during pressurization of the system by means of the squeeze bulb, air escaping from by-pass aperture 41 to pressurize lower chamber 40 will have been fully exhausted into upper chamber 52 through aperture 53 before the overflow or excess liquid reaches aperture 53. This sequencing prevents the splattering of large particles up into the upper reservoir by air passing through aperture 53. Moreover, a baffle 54 is disposed above aperture 53 as a further safeguard against the spitting of large particles into upper chamber 52.

During the spraying portion of the cycle, outside air may be entrained into aspirator port 50 to comingle with the spray output being discharged through spray discharge horn 46.

FIG. 4 illustrates a more compact variation of the embodiment shown in FIG. 3. In this embodiment, the entire outer structure, or at least lower chamber 40', is fabricated from a flexible material such that when it is squeezed by the user, the accompanying pressure rise within lower chamber 40' serves to pressurize atomizing plenum 43' as well as to force liquid from chamber 40' into upper chamber 52'.

This embodiment functions in a manner identical to that described with reference to FIG. 3 when operating with the so-called closed squeeze bulb (i.e., a squeeze bulb without an inlet checkvalve). Since by-pass port 41 is eliminated in the FIG. 4 embodiment, it is necessary that the size of return port 53' be small enough to maintain adequate pressure for atomization within plenum 43'. A relatively small return port 53' in this embodiment can be tolerated because of the vigorous suction of liquid into lower chamber 40' upon release of flexible lower chamber 40'. Restricted aperture 53' serves the same purpose in providing the proper airflow distribution and pressure balance to the overall system that by-pass port 41 does in conjunction with the variation shown in FIG. 3.

In cases where a more viscous medicant or liquid is to be dispensed, and especially where it is desirous to atomize the liquid at the highest possible pressure, return port 53' may be located in partition 49' adjacent the wall of the sprayer. When lower chamber 40' is squeezed, the side walls are forced inwardly as shown by the dotted lines in FIG. 4. This squeezing action serves to mechanically close off return aperture 53' during the pressure cycle of operation so that virtually all of the pressure developed in lower chamber 40' is available to pressurize plenum chamber 43' and lift liquid from lower chamber 40' to upper chamber 52' via lift tube 45' and extension conduit 48'.

This embodiment as described earlier is particularly advantageous when the substance to be sprayed is viscous or sticky since return port 53' can then be made as large as necessary to ensure that there is a nonclogging flow back of liquid into lower chamber 40' during the suction or off-spraying portion of the cycle when the side walls of the sprayer are released. Since the closing and opening of return port 53' is accomplished by the mechanical action of the user as he squeezes and releases the resilient or flexible walls of the sprayer, the system is very reliable and has no internal moving parts. This is in contrast to mechanical checkvalves which are activated by a change in pressure, and whose small moving parts are often prone to clogging. The FIG. 4 embodiment is also very well suited to a nasal mist sprayer because of the vertical spray pattern it produces. It is also contemplated that for such uses, outlet 46' be provided with a means for regulating the spray output capacity and particle size, similar to the function provided by revolvable or push/pull collar 57 in FIG. 3.

EMBODIMENT OF FIGS. 5, 6, and 9

FIGS. 5 and 6 illustrate a further embodiment of the present invention which is particularly adapted as a respiratory rhythm atomizer. The device includes a housing having upper and lower chambers 101 and 102 with partition 108 therebetween. Both the liquid to be atomized and the hollow plenum 103 containing aperture 104 are disposed in the lower chamber 101. The partition 108 is provided with a drain opening 109 and is traversed by a liquid lift tube 106 having an upper, discharge end disposed above the partition 108 and a lower end disposed at a low point in chamber 101 and immersed in the liquid supply. The lower chamber 101 is provided with an upwardly curved inhalation tube 112 which terminates in a disposable mouthpiece 110. The upper chamber 102 is vented to atmosphere via arrestor tube 115 affixed to vent port 114 provided in the top or other suitable location therein, to allow the outgassing of air, while preventing the carry-over of large liquid particles.

FIG. 9 illustrates a disposable nosepiece 110.

Plenum 103 is supplied with gas under pressure via conduit 111 having an open end disposed externally of the chamber 101. An impactor 105 is preferably positioned in the path of gas flow through aperture 104 in plenum 103.

Apparatus constructed according to this embodiment is preferably used in the same manner as the apparatus shown in FIGS. 1 and 2. However, in using the earlier described atomizer shown in FIGS. 1 and 2, it is preferred that the patient simply inhale the desired amount of mist and then remove the mouthpiece from his mouth. Even though the patient can exhale into the inhalation medicant nebulizer, if he does so forcefully, he can blow the liquid medicant out of the vent tube and the aspirator control. In contrast, with the apparatus as shown in FIGS. 5 and 6, the unit is designed specifically to be held in the patient's mouth throughout the treatment period but without the disadvantage just noted. It is further designed to operate with either a continuous compressed gas source or with a conventional squeeze bulb.

Consider first the case where compressed gas such as air or oxygen is supplied to fitting 111 while mouthpiece 110 is placed in the patient's mouth. A jet of high pressure gas escapes from orifice 104 in plenum 103 and causes the pressure in lower chamber 101 to rise. This pushes liquid up into upper chamber 102 via lift tube 106 which has a downwardly curved upper end 113, as a result at which liquid is directed downwardly into the upper reservoir 102 to prevent splashing or splattering of large particles through vent port 114 and arrestor tube 115.

As long as the patient does not inhale (i.e., he may hold his breath or exhale) a positive pressure will be maintained in lower reservoir 101 and liquid will continue to flow up tube 106 and into upper chamber 102 which is always vented to atmosphere via vent port 114. As soon as the patient inhales, or should he even remove mouthpiece 110 from the mouth, the pressure within the lower chamber 101 will drop to atmospheric pressure or below, and liquid will begin to flow from upper chamber 102 to lower chamber 101 through aperture 109, in partition 108. Since plenum 103 is disposed in lower chamber 101 directly below aperture 109, the liquid draining into lower chamber 101, will spread over plenum 103 in a continous thin film that is ideally prepared for spraying. Gas escaping from orifice 104 ruptures said thin film and causes a continuous dispersion of fine liquid particles so long as there is a drain back of liquid from upper chamber 102 into lower chamber 101 through aperture 109.

In FIGS. 5 and 6, an impactor 105 is shown located in front of orifice 104 and while not a necessary component to the operation of the unit, it will help to produce a very fine aerosol of the type preferred in inhalation therapy applications.

The high quality aerosol passes through the inhalation tube 112 which has the general shape of a calabash type smoking pipe. By causing the aerosol to make two right angle bends, before it leaves mouthpiece 110 and enters the patient's mouth, it can be assured that all large particles have been eliminated in the tortuous path that the aerosol must follow as it passes through inhalation tube 112.

To recharge the upper reservoir with liquid, the patient has only to place mouthpiece 110 in his mouth, and the cycle just described will be repeated. In most cases, the patient will hold mouthpiece 110 in his mouth throughout the entire treatment and will alternately inhale to receive mist and exhale to assist in the pumping of liquid from the lower chamber 101 to upper chamber 102.

Aperture 109 in partition 108 is sized so that during the exhalation phase of operation, gaseous bubbles stream upwardly through aperture 109 acting as a closure means to prevent the flow of liquid down over atomizing plenum 103 and since lower chamber 101 has a higher internal pressure than upper chamber 102, no mist is produced. The gas or air that enters upper chamber 102 in this manner via aperture 109 bubbles through the liquid being retained in upper reservoir 102 and outgases to the atmosphere through vent port 114 which has an arrestor tube 115 to capture any large particles of liquid that might tend to be carried overboard by the venting of gas as just described.

The entire operation just described can also be carried out with the use of a simple squeeze bulb. However, in this case, the patient must exhale or blow into mouthpiece 110 to force the liquid in lower chamber 101 up into upper chamber 102. The pressure generated by the squeeze bulb alone, while sufficient to atomize the fluid, is not sufficient to pressurize lower chamber 101 to the extent that liquid will be driven completely up lift tube 106. Once the patient has blown the liquid from chamber 101 up into chamber 102, he obtains mist by simultaneously inhaling while depressing the squeeze bulb.

EMBODIMENT OF FIG. 7

In FIG. 7 there is disclosed a further embodiment of the present invention. This embodiment is similar to that shown in FIGS. 5 and 6 with certain modifications especially designed to provide an intermittent hand sprayer to dispense liquids in a spray similar to that produced by a conventional aerosol spray can. Accordingly, the unit has no impactor and utilizes a straight, short discharge horn 212.

This intermittent hand sprayer operates with a conventional squeeze bulb 216 located between tube 215 and air inlet tube 211. Tube 215 is attached to the suction side of the squeeze bulb 216 which contains a purely conventional mechanical check valve 217, while air inlet tube 211 is attached to the pressure side of the squeeze bulb.

When the squeeze bulb 216 is depressed for the first time, air escapes through orifice 204 in plenum 203. When the squeeze bulb is released for the first time, air from upper chamber 202 is drawn into squeeze bulb 216 via tube 215 and mechanical check valve 217 incorporated in the squeeze bulb 216. This creates a vacuum in upper chamber 202 such that liquid from lower chamber 201 is drawn into upper chamber 202 through the candy-cane shaped lift tube 206. The vacuum thus created in upper chamber 202 holds liquid in the upper chamber 202 until the squeeze bulb 216 is depressed for the second time. When this happens, the jet pump action of the gas escaping from orifice 204 in plenum 203 reduces the pressure within lower chamber 201 to the extent that the liquid previously captured in upper reservoir 202 begins to flow over plenum 203, where it can be dispersed by the air escaping from orifice 204 in hollow plenum 203. Also it is believed that the flow of liquid from upper chamber 202 to lower chamber 201 is enhanced during pressurization of plenum 203 by a slight leakage of air past checkvalve 217 contained in squeeze bulb 216.

When the squeeze bulb 216 is released for the second time, a new charge of liquid is sucked into the upper reservoir 202 and this new charge is subsequently drained over the atomizing plenum 203 during the next pressure manipulation of the squeeze bulb 216.

This intermittent cycle of mist will continue until all but a very small amount of liquid (e.g., 1 or 2 cc's) is exhausted. By properly sizing aperture 209 in partition 208, the charge of liquid being sucked into the upper reservoir 202 can be made to equal or be slightly less than the amount of liquid that drains into the lower reservoir with each pressure manipulation of the squeeze bulb. To further ensure good drainage from upper chamber 202 to lower chamber 201, a small bleed-off orifice 218 may also be installed in any convenient location in upper chamber 202. This very small orifice is not large enough to destroy the vacuum in upper chamber 202 during the rapid suction phase of operation when liquid is quickly drawn into the upper chamber. However, on the other hand, bleed-off orifice 218 is large enough to insure a sufficient flow of atmospheric air into upper chamber 202 to break the vacuum in said upper chamber during the time when plenum 203 is being pressurized. Bleed-off orifice 218 also ensures that there is complete liquid drain back into lower chamber 201 when the unit is not in use.

The squeeze bulb is located as an exterior component to the main body of the spray unit. However, it is fully contemplated that the components of the intermittent hand sprayer shown in FIG. 7 could be rearranged such that the squeeze bulb is made an integral part of the system with its suction side communicating with upper chamber 202, while the pressure side of the squeeze bulb communicates with the interior of plenum 203.

EMBODIMENT OF FIG. 8

Figure 8:
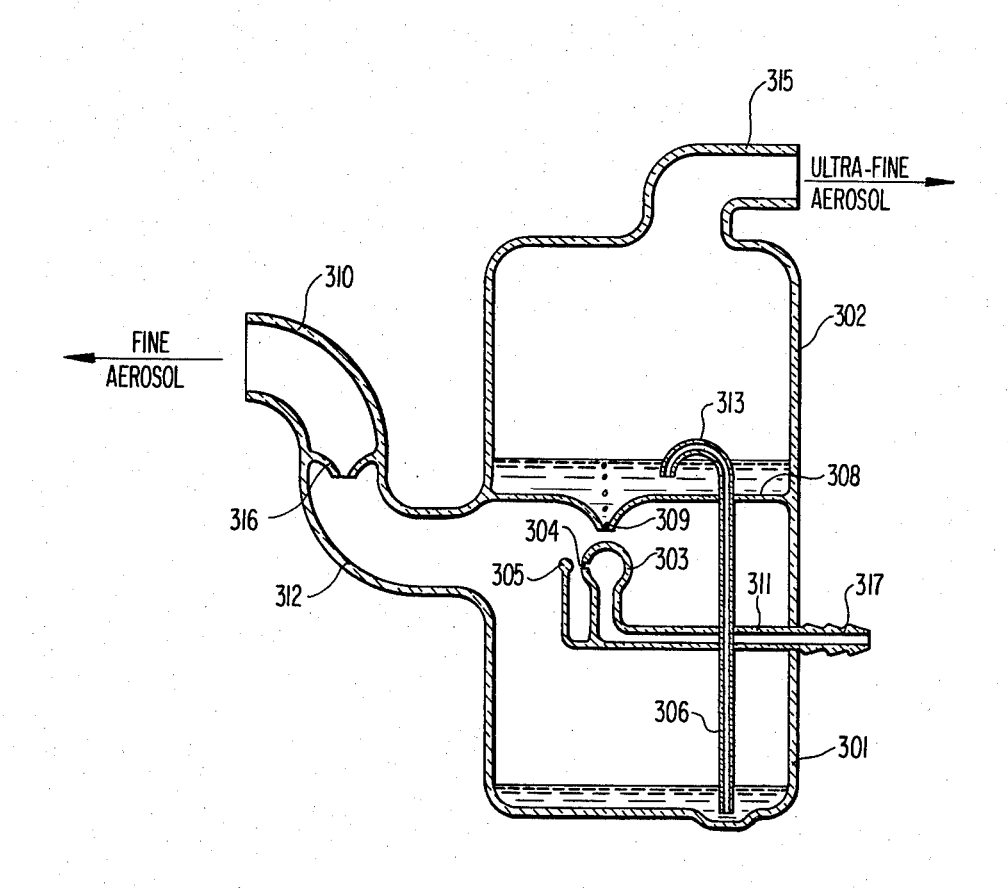

FIG. 8 illustrates an embodiment especially designed as a continuous dual spray atomizer or nebulizer to produce two different aerosol streams. In the embodiments previously described, the spray produced is intermittent in nature, that is, the devices produce a spray during only a portion of the total operating cycle. In FIG. 8, there is shown an upper chamber 302, a lower chamber 301, a partition 308 separating the two chambers, a lift tube 306 with a curved upper end 313, a plenum 303 having an aperture 304 disposed in lower chamber 301, means to supply gas under pressure via conduit 311 and fitting 317 to the plenum chamber, means for creating a pressure differential between the chambers, and outlet passages 310 and 315 disposed in chambers 301 and 302, respectively.

By proper sizing of orifice 309 in partition 308, and by installing a flow restrictor 316 in the main discharge horn 312, the embodiment is capable of producing not only one continuous mist, but is capable of providing two streams of aerosol eminating from the same atomizing plenum 303.

A unique feature of this embodiment is that the flow of aerosol leaving the upper chamber 302 has a particle size which is substantially less than that leaving the lower chamber 301. This dual function is accomplished by placing an area restrictor 316 in the outlet horn 312, which is affixed to lower chamber 301. This restrictor 316 acts to maintain a slightly higher pressure in the lower chamber 301 than in upper chamber 302. When a continuous gas source is supplied to fitting 317, which in turn communicates with plenum 303 via conduit 311, the slightly higher pressure created in lower chamber 301 causes the liquid in lower chamber 301 to be forced into upper chamber 302 via candy-cane-shaped lift tube 306. However, because aperture 309 in partition 308 is sized relatively large, liquid flows from upper chamber 302 into lower chamber 301 despite the fact that the pressure within lower chamber 301 is higher than that in chamber 302 and in spite of the fact that there is a stream of air bubbles passing upwardly into chamber 302 from chamber 301 through aperture 309.

Accordingly, there is a simultaneously opposing flow of liquid and gas passing through aperture 309. This causes a spray to be discharged from exit 310 of lower discharge horn 312. However, since the pressure in lower chamber 301 is greater than that in upper chamber 302, some of the mist produced in the lower chamber is carried up into the upper chamber with the gas bubbling through aperture 309 in partition 308. At the same time, additional mist also passes from the lower chamber to the upper chamber, via lift tube 306. This occurs because the positive pressure in lower chamber 301 has forced virtually all of the liquid that was initially present in the lower chamber 301 into upper chamber 302. There also continues to be a flow of small amounts of drainoff liquid from the base of plenum and this liquid is continually forced into upper chamber 302. Since, in this steady-state mode of operation, lift tube 306 is only partially filled with liquid, it provides a conduit for the aerosol in lower chamber 301 to be transported to a region of lower pressure namely upper chamber 302 along with small amounts of liquid that are continually passed into upper chamber 302.

Since the bottom of upper chamber 302 is covered with liquid, the mist entering upper chamber 302 via aperture 309 and lift tube 306, must bubble up through said liquid in the upper chamber before being discharged through upper discharge horn 315.

During passage through the liquid bath, all of the larger particles are entrapped in the liquid with the result that the mist leaving upper discharge horn 315, is much finer than that leaving lower discharge horn 310, even though the same atomizer is supplying the mist that is eminating from both discharge horns. The liquid in the upper reservoir acts in a manner to filter the mist leaving said upper reservoir. In the steady-state operating mode of this spray device, the full liquid load is maintained in the upper reservoir, while a very small flow of liquid is supplied to the atomizing surface. The excess flow or runoff, from the base of the atomizing plenum, is then conveyed up through lift tube 306 to resupply the upper reservoir with liquid.

In the figures described hereinabove, the plenum has been shown as spherical or bullet shape merely for the sake of convenience. It should be understood, however, that other shapes may be used. The plenum chamber need only have an outer surface which is sufficiently smooth and preferably convex and curved to allow liquid to flow over its outer surface in a thin film and to pass over a small aperture.

With respect to the materials employed, it is preferred that they be nonporous and noncorrosive and have a surface that is nonabsorptive. Moreover, for many applications, it is desirable to employ materials which can withstand relatively high temperatures and are relatively durable so as to minimize breakage. It has been found that glass and certain plastics such as polycarbonates, polyacrylates and polypropylene are especially suitable for the purposes of the present invention.

Having described the basic concept and various embodiments of the invention in several operative configurations, it will become readily apparent that various changes and modifications will occur to those skilled in the art and that such modifications and changes fall within the spirit and scope of the inventive concept as defined in the appended claims.

What is claimed is:

1. Apparatus for producing a finely divided liquid spray comprising:
   a first chamber for holding a supply of liquid;
   a second chamber;
   first means for conveying liquid from the first chamber to the second chamber;
   second means distinct from the first means for conveying the liquid from the second chamber back to the first chamber;
   means for producing alternately and repetitively a first pressure differential and either a second different opposite pressure differential or pressure balance between said first and second chambers, said first pressure differential causing the flow of liquid from said first chamber to said second chamber and said second pressure differential or pressure balance causing the flow of said liquid from said second chamber back to said first chamber;
   a hollow plenum chamber having a smooth outer surface over at least a portion thereof and so disposed in the flow path of said liquid as it moves from said first chamber to said second chamber and back to said first chamber as to have at least a portion of the liquid impinge upon its outer surface;
   said plenum chamber defining therein at least one through aperture;
   means for supplying gas under pressure to the interior of the plenum chamber to exit through said aperture; and
   outlet means for exiting of the finely divided liquid particles from the apparatus.

2. The apparatus of claim 1 wherein said hollow plenum chamber is located in said first chamber so as to receive the flow of liquid from said second chamber to said first chamber via said second means.

3. The apparatus of claim 1 wherein said plenum chamber is located in said chamber so as to receive the flow of liquid from said first chamber to said second chamber.

4. The apparatus of claim 1 wherein said second means for conveying liquid from the second chamber back to the first chamber includes a closing means for blocking said second means during at least a portion of that part of the operating cycle when liquid is conveyed from said first chamber to said second chamber.

5. The apparatus of claim 4 wherein said second means is closed during at least a portion of that part of the operating cycle when liquid is conveyed from said first chamber to said second chamber, and open when liquid is conveyed from said second chamber to said first chamber.

6. The apparatus of claim 5 wherein said second means is closed by distorting the walls of said first chamber, and said second means is opened by allowing said distorted walls to return to their original configuration.

7. The apparatus of claim 1 wherein gas is allowed to pass from said first chamber to said second chamber via said second means at the same time that liquid is passing from said first chamber to said second chamber via said first means.

8. The apparatus of claim 1 wherein said means for producing a pressure differential is manually operable.

9. The apparatus of claim 8 wherein said means for producing said differential pressure is a squeeze bulb.

10. The apparatus of claim 8 wherein said means for producing said differential pressure causes a reduction in volume within said first chamber.

11. The apparatus of claim 1 wherein said means for providing pressure differential comprises a vacuum means in said second chamber.

12. The apparatus of claim 1 wherein said means for providing pressure differential pressurizes said first chamber.

13. The apparatus of claim 12 wherein said means for providing a pressure differential comprises a squeeze bulb affixed to said first chamber.

14. The apparatus of claim 12 wherein said first chamber is made of a resilient flexible material adapted to be manually squeezed to pressurize said first chamber.

15. The apparatus of claim 12 wherein said second means for conveying liquid from the second chamber back to the first chamber includes a closure means for blocking said second means during at least a portion of that part of the operating cycle when liquid is conveyed from said first chamber to said second chamber and wherein said first chamber is made of a resilient flexible material adapted to be manually squeezed to pressurize said first chamber, and to pressurize the interior of the plenum chamber, and to close off said closure means.

16. The apparatus of claim 15 which further includes a partition separating said first and second chambers, and wherein said second means comprises a port located adjacent a wall of the apparatus.

17. The apparatus of claim 16 wherein said outlet means is located above said plenum chamber for exiting of said liquid particles vertically upward from the apparatus.

18. The apparatus of claim 1 wherein said means for supplying gas under pressure to the interior of the plenum chamber is manually operable.

19. The apparatus of claim 1 wherein the same source of gas supplies both said means for providing a pressure differential and said means for supplying gas under pressure to the interior of the plenum chamber.

20. The apparatus of claim 19 wherein said source is manually operable.

21. The apparatus of claim 20 wherein said manual operation is carried out by squeezing or distorting said first chamber.

22. The apparatus of claim 1 which further includes a partition between said first and said second chambers.

23. The apparatus of claim 22 wherein said second means for conveying liquid from said second chamber to said first chamber comprises an aperture in said partition.

24. The apparatus of claim 1 wherein said first means for conveying liquid from the first chamber to said second chamber comprises hollow conduit means.

25. The apparatus of claim 1 wherein said means for producing said pressure differential comprises vacuum means in said second chamber; wherein said plenum is located in said second chamber; and wherein said first chamber contains a port vented to the atmosphere.

26. The apparatus of claim 25 wherein said port further includes an aspirator having control means to vary the flow area of said port.

27. The apparatus of claim 1 wherein said plenum chamber is located in said second chamber, wherein said means for producing said pressure differential comprises superatmospheric pressure in said first chamber wherein said means for supplying gas under pressure to the interior of said plenum chamber is also in communication with said first chamber.

28. The apparatus of claim 27 wherein said second chamber further includes a port in communication with the atmosphere.

29. The apparatus of claim 27 wherein superatmospheric pressure in said first chamber is provided by the output flow from a conventional respirator or ventilator.

30. The apparatus of claim 27 wherein said means for supplying gas under pressure comprises a squeeze bulb.

31. The apparatus of claim 1 wherein said plenum chamber is located in said first chamber, wherein said means for producing said pressure differential comprises means for alternating between superatmospheric pressure in said first chamber for conveying liquid from said first chamber to said second chamber, and atmospheric pressure for conveying liquid from said second chamber back to said first chamber.

32. The apparatus of claim 31 which further includes a port in said second chamber in communication with the atmosphere.

33. The apparatus of claim 31 which comprises means connected to said port for preventing large liquid particles from exiting the apparatus.

34. The apparatus of claim 1 wherein said plenum chamber and said outlet means are located in said first chamber, and wherein the suction side of a squeeze bulb communicates with said second chamber while the pressure side of said squeeze bulb communicates with the interior of said hollow plenum chamber, for providing said liquid flow path upon alternately squeezing and releasing said bulb, and also for providing compressed gas for atomization.

35. The apparatus of claim 34 which further comprises a small vent hole in said second chamber for aiding in conveying liquid from said second chamber back to said first chamber.

36. The apparatus of claim 1 in which further comprises impactor means positioned in the path of the gas discharge from said plenum chamber for further reducing the size of the liquid particles.

37. The apparatus of claim 1 wherein said plenum chamber is located in said second chamber so as to receive the flow of liquid from said first chamber to said second chamber and wherein said through aperture is disposed at the high point of said hollow plenum.

38. The apparatus of claim 37 which further comprises means to adjust said first means for conveying liquid so as to direct the flow of liquid against the outer surface of said hollow plenum at any desired location below said through aperture.

39. The apparatus of claim 37 wherein said outlet means is located above said plenum chamber for exiting of said liquid particles vertically upward from the apparatus.

40. The apparatus of claim 1 which further comprises means to vary the cross sectional area of said outlet means through which the finely divided liquid particles exit.

41. The apparatus of claim 1 wherein the length of said outlet means can be varied to control the quantity and quality of the particles exiting from said outlet means.

42. The apparatus of claim 1 wherein said plenum chamber is convexly curved.

43. The apparatus of claim 1 wherein said plenum chamber is spherical.

44. The apparatus of claim 1 wherein said plenum chamber is bullet shaped.

45. The apparatus of claim 1 wherein means for providing pressure differential between said first and second chambers comprises a mouth piece connected to said second chamber whereby inhalation of the user causes a vacuum in said second chamber.

46. The apparatus of claim 1 wherein means for providing a pressure differential between said first and second chambers comprises a nose piece connected to said second chamber whereby inhalation of the user causes a vacuum in said second chamber.

47. The apparatus of claim 1 whereby means for producing pressure differential between said first and second chambers includes means for inhibiting the liquid from being broken be gas bubbles prior to the liquid impinging on the outer surface of the plenum chamber.

48. A process for dispensing an aerosol to an individual which comprises placing in said individual's mouth or nose an apparatus for producing a finely divided liquid spray, said apparatus comprising:
a first chamber for holding a supply of liquid;
a second chamber;
first means for conveying liquid from the first chamber to the second chamber;
second means distinct from the first means for conveying the liquid from the second chamber back to the first chamber;
means for producing alternately and repetitively a first pressure differential and either a second different opposite pressure differential or pressure balance between said first and second chambers, said first pressure differential causing the flow of liquid from said first chamber to said second chamber and said second pressure differential or pressure balance causing the flow of said liquid from said second chamber back to said first chamber;
a hollow plenum chamber having a smooth outer surface over at least a portion thereof and so disposed in the flow path of said liquid as it moves from said first chamber to said second chamber and back to said first chamber as to have at least a portion of the liquid impinge upon its outer surface;
said plenum chamber defining therein at least one through aperture;
means for supplying gas under pressure to the interior of the plenum chamber to exit through said aperture; and
outlet means for exiting of the finely divided liquid particles from the apparatus.

49. The process of claim 48 whichfurther comprises inhaling by the said individual to thereby produce vacuum means in said second chamber.

50. A method for producing a finely divided liquid spray comprising:
providing a supply of liquid in a first chamber;

alternatively and repetitively generating a pressure differential between said first chamber and a second chamber to convey said liquid from said first chamber to said second chamber, and either a second different opposite pressure differential or pressure balance between said first chamber and said second chamber to convey said liquid back to the first chamber to provide flow over a predetermined flow path;

directing the flow path of at least a portion of said liquid at is flows over its said flow path so as to impinge upon a smooth outer surface of a hollow plenum chamber having at least one aperture therein so that the liquid flows as a thin film over said at least one aperture;

supplying gas under pressure to the interior of said plenum chamber;

causing said gas to escape through at least one aperture in said plenum chamber to thereby rupture said film as the liquid flows over said at least one aperture and cause dispersion of finely divided liquid particles; and permitting said finely divided liquid particles to exit from at least one of said first chamber or said second chamber.

51. The method of claim 50 wherein the step of producing a pressure differential is created by pressurizing said first chamber for only a limited time interval during wherein liquid flows from said first chamber to said second chamber; and permitting return flow from said second to said first chamber only after the termination of said pressurization.

52. The method of claim 50 which comprises producing said pressure differential and supplying gas under pressure to the interior of said plenum chamber from the same source of manual operation and to thereby produce an intermittent spray.

53. The method of claim 52 wherein said manual operation is by squeezing action to produce a spray upon said squeezing and to cause discontinuence of said spray upon release of the squeezing action.

54. The method of claim 50 wherein during the time when said liquid is flowing over said at least one aperture the pressure in the chamber containing said plenum chamber is no greater than the pressure in the other chamber.

* * * * *